(12) United States Patent
Ding et al.

(10) Patent No.: US 7,468,396 B2
(45) Date of Patent: Dec. 23, 2008

(54) PROCESS FOR DIRECTLY PRODUCING MIXED LINEAR ALPHA-ALCOHOLS HAVING 1 TO 18 CARBON ATOMS FROM SYNTHESIS GAS

(75) Inventors: Yunjie Ding, Dalian (CN); Hejun Zhu, Dalian (CN); Tao Wang, Dalian (CN); Guiping Jiao, Dalian (CN); Yuan Lv, Dalian (CN)

(73) Assignee: Dalian Institute of Chemical Physics, Chinese Academy of Sciences, Dalian (CN)

(*) Notice: Subject to any disclaimer, the term of this patent is extended or adjusted under 35 U.S.C. 154(b) by 0 days.

(21) Appl. No.: 11/890,772

(22) Filed: Aug. 6, 2007

(65) Prior Publication Data

US 2008/0293835 A1 Nov. 27, 2008

(30) Foreign Application Priority Data

May 24, 2007 (CN) .................. 2007 1 0099553

(51) Int. Cl.
*C07C 27/00* (2006.01)

(52) U.S. Cl. .................. 518/715; 518/700; 568/840
(58) Field of Classification Search .................. 518/715, 518/700; 568/840
See application file for complete search history.

(56) References Cited

U.S. PATENT DOCUMENTS

| | | | |
|---|---|---|---|
| 4,298,354 A | 11/1981 | Hardman et al. | |
| 4,504,600 A | 3/1985 | Wright et al. | |
| 4,675,344 A | 6/1987 | Conway et al. | |
| 4,725,626 A | 2/1988 | Graham et al. | |
| 4,749,724 A | 6/1988 | Quarderer et al. | |
| 4,751,248 A | 6/1988 | Lin et al. | |
| 4,752,623 A | 6/1988 | Stevens et al. | |
| 4,775,696 A | 10/1988 | Prada-Silva et al. | |
| 4,780,481 A | 10/1988 | Courty et al. | |
| 4,831,060 A | 5/1989 | Stevens et al. | |
| 4,882,360 A | 11/1989 | Stevens | |
| 6,248,796 B1 | 6/2001 | Jackson et al. | |
| 6,753,353 B2 | 6/2004 | Jackson et al. | |
| 6,765,025 B2 * | 7/2004 | Ding et al. .................. 518/715 |

OTHER PUBLICATIONS

Anderson, R.B. et al. (1952) "Synthesis of Alcohols by hydrogenation of carbon monoxide" *Industrial and Engineering Chemistry* 44:2418-2424.
Behr, A.. et al. (1996) "Ziegler Processes" Ed. Ullmann's *Encyclopedia of Industrial Chemistry*, 5th Ed. A28:505-508.
Diffenbach et al. (1982) "Synthesis gas conversion to liquid fuels using promoted fused iron catalysts" *Fossil Fuels* 96:106913X.
Diffenbach et al. (1981) "Synthesis gas conversion to liquid fuels using promoted fused iron catalysts" U.S. Department of Commerce, National Technical Information Service, pp. 1-66.
Hardman et al. (1980) "Alcohols from synthetic gas" EPO application 5,492 *Chemical Abstracts* 92:166257p.
Kroschwitz, J.I. et al. (1996) "Alcohols, Higher Aliphatic" Ed. *Encyclopedia of Chemical Technology*, 4th Ed., vol. 1, John Wiley & Sons, New York, p. 894-903.

* cited by examiner

*Primary Examiner*—Elvis O Price
(74) *Attorney, Agent, or Firm*—Knobbe Martens Olson & Bear LLP

(57) ABSTRACT

The invention provide a process for producing directly mixed linear alpha-alcohols having 1 to 18 carbon atoms from synthesis gas comprising hydrogen and carbon monoxide, comprising the step of reacting hydrogen and carbon monoxide over a catalyst to produce mixed linear alpha-alcohols having 1 to 18 carbon atoms and hydrocarbons having 1 to 25 carbon atoms through Fischer-Tropsch process in one step in a reactor, wherein: the mole ratio of hydrogen to carbon monoxide is within the range of 1 to 3; the catalyst is an activated carbon supported cobalt based catalyst; the reactor is a fixed bed reactor, a slurry reactor or a fluid reactor; the reaction is carried out under specific conditions.

7 Claims, 1 Drawing Sheet

PROCESS FOR DIRECTLY PRODUCING MIXED LINEAR ALPHA-ALCOHOLS HAVING 1 TO 18 CARBON ATOMS FROM SYNTHESIS GAS

CROSS-REFERENCE TO RELATED APPLICATIONS

This applications claims the benefit of Chinese application No. 200710099553.7, filed May 24, 2007.

FIELD OF THE INVENTION

The invention relates to a process for directly producing mixed linear alpha-alcohols having 1 to 18 carbon atoms and paraffins having 1 to 21 carbon atoms. The former is useful as intermediates of detergents, plasticizers, lubricants or surfactants, and useful as additives of gasoline having octane number, and diesel having high cetane number. And the latter is useful as diesel fuels with sulfur-free, nitrogen-free or aromatics-free, and useful as naphtha with aromatics-free. More particularly, the invention relates to a process for preparing directly mixed linear alpha-alcohols and the middle distillates from synthesis gas over an activated carbon supported cobalt based catalyst that cut off the heavier end of the Schultz-Flory distribution.

BACKGROUND OF THE INVENTION

The search for processes to provide alternate feedstocks for fuels and chemicals, and particularly high quality diesel fuels and high value mixed linear alpha-alcohols, has been prompted due to the potential shortage of traditional petroleum reserves, and the increasing instability of international hydrocarbon resources.

Oil fields typically have deposits of natural gas associated with them. In remote locations where natural gas transportation may not be economically attractive, gas conversion technology can be used for chemically converting natural gas to higher molecular weight hydrocarbons. Current gas conversion technologies rely on the chemical conversion of natural gas to synthesis gas, which is a mixture of carbon monoxide and hydrogen. Synthesis gas is then reacted in a catalyzed hydrocarbon synthesis process commonly known as Fischer-Tropsch synthesis.

In 1923, Fischer-Tropsch synthesis process was provided, with the discovery of an efficient catalyst to convert synthesis gas into hydrocarbons mixtures. Coal-based synthetic fuels was produced during the World War II in Germany, and later in South Africa (SASOL), and the energy crisis of 70's and 80's renewed the interest toward the conversion of the increasing remote natural gas reserves to liquid fuel (GTL).

Alpha-alcohols containing 6 to 20 carbon atoms are useful as intermediates for the synthesis of plasticizers, detergents, lubricants and other surfactants. Therefore, processes for making mixed linear alpha-alcohols which comprises reacting a gaseous mixture of carbon monoxide and hydrogen in presence of an activated cobalt based catalyst are of commercial interest.

Generally speaking, mixed linear alpha-alcohols are often made through several steps, see for instance B. Elvers, et al., Ed., Ullmann's *Encyclopedia of Industrial Chemistry*, 5th Ed., Vol. A28, 1996, p. 505-508 and references therein, and J. I. Kroschwitz, et al., Ed, *Encyclopedia of Chemical Technology*, 4th Ed., Vol. 1, John Wiley & Sons, New York, p. 894-903 and references therein, both of which are hereby incorporated herein by reference.

There are two processes for the production of synthetic linear alcohols which are (a) ALFOL® process and EPAL® process, based on the work of Prof. Dr. Ziegler using organic aluminum compounds and (b) the oxo-process (hydroformylation). The former process involves five steps: hydrogenation, ethylation, growth reaction, oxidation and hydrolysis, and the latter process consists of the reaction of olefins with a H2/CO gas mixture, in the presence of a suitable catalyst, wherein alpha-olefins yield approximately equal amounts of linear and branched aldehydes, and linear and branched alkenes can be used in this process due to double-bond being isomerized in the presence of the same catalyst. For a long time, paraffin-based process was predominant for the production olefins, especially used for detergents, now ethylene has became a preferable raw material. The principal steps in oxo-process are ethylene oligomerization, isomerization and metathesis.

Almost as old as the Fischer-Tropsch process for making hydrocarbons is the Fischer-Tropsch process for making alcohols. The Fischer-Tropsch process is carried out by passing a mixture of CO and $H_2$ over a catalyst for the hydrogenation of carbon monoxide. Numerous catalysts and catalytic methods have been studied in attempt to provide a viable method for the production of aliphatic alcohols from synthesis gas.

Three main types of processes have been proposed for preparing alcohols from gaseous mixtures comprising carbon monoxide and hydrogen. One of these is a modified Fischer-Tropsch process which involves the use of alkali metal-containing iron based catalysts. Generally, this process suffers from poor selectivity and low productivity. Another process is the iso-butyl synthesis as used in Europe between 1935 and 1945. This process is analogous to the methanol synthesis process and utilizes a similar catalyst, i.e. zinc chromite, modified by addition of an alkali metal salt, at high temperature and high pressure. Typically, the main products from this process comprise methanol (50%), ethanol (20-40%), n-propanol and higher alcohols which are predominantly non-linear primary and secondary alcohols. The third process was originally assigned to Dow Chemical Company, in which primarily C1 to C4 mixed alcohols are produced in good yield over a supported catalyst based on molybdenum disulfide.

A typical review article related to alcohols preparation is R. B. Anderson et al. "Industrial and Engineering Chemistry" vol. 44, No. 10 pp. 2418-2424. A number of catalysts containing zinc, copper, chromium, manganese, thorium and iron, occasionally promoted with alkali or other materials for making various alcohols are listed in this article.

U.S. Pat. No. 4,504,600 provides a CO hydrogenation process for producing alcohols utilizing thallium-promoted iron-based catalysts. A mixture of CO and $H_2$ is selectively converted to liquid C6~C12 hydrocarbon containing C6~C12 alcohols in an amount of 4~8 wt. %, and methane in an amount of 1 wt. % relative to the total produced hydrocarbons, with a CO2 selectivity of 12~18 mol. %.

U.S. Pat. No. 4,780,481 describes a process for manufacturing a mixture of saturated primary alcohols by reacting carbon monoxide with hydrogen in the presence of a catalyst formed essentially of copper, cobalt and zinc, promoted by alkali and alkaline earth metals and optionally zirconium and rare earth metals.

U.S. Pat. No. 4,725,626 discloses a catalyst and a process for the production of alcohols from CO and $H_2$. The catalyst has the formula: $RuCuaMbAcN_2O_x$, wherein A is an alkali metal or an alkaline earth metal or mixture thereof, and M is Mo or W or mixtures thereof.

U.S. Pat. No. 4,751,248 discloses a process for converting synthesis gas ($H_2$/CO) to aliphatic alcohols containing at least 2 carbon atoms, comprising the steps of passing the synthesis gas first through a catalyst zone comprising wherein the catalyst comprises (a) Co metal and/or Co oxide and (b) MgO and/or ZnO (preferably MgO), and then through a catalyst zone wherein the catalyst comprises (c) Cu metal and/or Cu oxide and (d) ZnO.

U.S. Pat. No. 4,749,724 describes a process for forming an alcohol fraction boiling in the boiling range of motor gasoline that is enriched in higher alcohols, comprising the step of contacting containing a mixture of $H_2$ and CO, and a lower alkanol with a catalyst comprising (1) molybdenum, tungsten or a mixture thereof in free or combined form; (2) an alkali or alkaline earth element; (3) a support.

EPO application 79-5,492 (Chemical Abstracts 92:166, 257b), Hardman et al., discloses the production of alcohols using a 4-component catalyst, wherein the four components are copper, thorium, an alkali metal promoter, and a specific metal such as molybdenum. Chemical Abstracts 96:106,913x, Diffenbach et al., disclose a nitrided iron catalyst which is promoted by molybdenum for making alcohols from synthesis gas.

All of the aforementioned references are hereby incorporated herein by reference.

U.S. Pat. Nos. 4,675,344 and 4,775,696 state that a method for controlling the ratio of methanol and higher alcohols produced in a process for making mixed alcohols by contacting a $H_2$/CO mixture with a catalyst which contains molybdenum, tungsten or rhenium, said method comprising adjusting the concentration of a sulfur releasing substance in the feedstock.

U.S. Pat. Nos. 4,752,623, 4,831,060 and 4,882,360 disclose a process for selectively making C1-C6 alcohols from synthesis gas, comprising the step of contacting a mixture of $H_2$/CO with a catalytic amount of a catalyst wherein the catalyst is consisted of (1) a catalytically active metal, such as molybdenum, tungsten or rhenium; (2) a co-catalytic metal, such as cobalt, nickel, or iron; (3) an alkali or alkaline earth metal; (4) an optional support. The catalyst has to be sulfidized before the contact.

More recently, U.S. Pat. Nos. 6,248,796 and 6,753,353 disclose a method for the production of mixed alcohols by using a sulfidized transition metal catalyst selected from Group VI B metals, such as molybdenum or tungsten; nanosizing the metal catalyst during its synthesis; suspending the catalyst in solvents to form a slurry; adding, a sulfur containing material to extend the catalyst life; and contacting this slurry with a mixture of CO and $H_2$.

Previous catalytic methods have been notably effective for converting CO and $H_2$ feedstocks into hydrocarbons and C1 to C6 alcohols, but none has been particularly effective for providing a substantial yield of a higher aliphatic C6 to C18 alcohols at a moderate temperature and pressure.

An extensive amount of works have been carried out in order to modify and improve the selectivity of a process for producing C6-C18 alcohols, especially C6-C18 linear alcohols, particularly under conditions that low methane and CO2 are produced. Such a process is desired since C6-C18 linear alcohols are industrially important and used in detergents, surfactants and plasticizers.

Thus far, no one has disclosed an activated carbon supported cobalt based catalyst which affords improved yields of mixed linear alpha-alkanols, naphtha distillates and diesel fuels from the reaction between carbon monoxide and hydrogen.

Naphtha is the most common feedstock sent to naphtha cracking units for the production of ethylene. A typical naphtha feedstock contains a mixture of paraffinic, naphthenic, and aromatic hydrocarbons with varied molecular weight and molecular structure. The compositions of naphtha feedstocks vary considerably, while the composition has a significant impact on ethylene and byproduct yields. Normal and branched paraffins convert to ethylene in a cracker, but the ethylene yield from n-paraffin is much greater than those from others. Naphtha is also used primarily as feedstocks for producing a gasoline component having high octane value via a catalytic reforming process. The naphtha distillates produced from Fischer-Tropsch process contains predominantly n-paraffins having 5 to 10 carbon atoms, which are excellent feedstocks for the production of ethylene.

Clean diesel fuels that contain no or almost no sulfur, nitrogen, or aromatics, are or will likely be demanded largely as diesel fuel or in blending diesel fuels. Clean diesel fuels with some mixed alcohols, having relatively high cetane number, are particularly valuable. Typical petroleum-derived distillates are not clean, in that they typically contain significant amounts of sulfur, nitrogen, and aromatics, and they have relatively low cetane numbers. Clean diesel fuels can be produced from petroleum-derived distillates through severe hydro-treating at great expense. The production of clean, high cetane number distillates from Fischer-Tropsch waxes has been discussed in the various literatures, but it is reported in few literatures that the catalyst can directly convert synthesis gas to diesel distillates with high quality or with some level mixed alcohols.

There is a need for a process by which mixed linear alpha-alkanols (C2-C18), naphtha distillates and diesel fuels with sulfur-free, nitrogen-free or aromatics-free can be directly synthesized from synthesis gas over an activated carbon supported cobalt based catalyst that cut off the heavier end of the Schultz-Flory distribution under moderate conditions.

SUMMARY OF THE INVENTION

After intensive study, the inventors find a process by which mixed linear alpha-alkanols ($C_2$-$C_{18}$), naphtha distillates and diesel fuels with sulfur-free, nitrogen-free or aromatics-free can be directly synthesized from synthesis gas over an activated carbon supported cobalt based catalyst that cut off the heavier end of the Schultz-Flory distribution under moderate conditions.

That is, the invention provides a process for producing directly mixed linear alpha-alcohols having 1 to 18 carbon atoms from synthesis gas comprising hydrogen and carbon monoxide, comprising the step of reacting hydrogen and carbon monoxide over a catalyst to produce mixed linear alpha-alcohols having 1 to 18 carbon atoms and hydrocarbons with high middle distillates content through Fischer-Tropsch process in one step in a reactor, wherein:

(a) the mole ratio of hydrogen to carbon monoxide is within the range of 1 to 3;

(b) the catalyst is an activated carbon supported cobalt based catalyst;

(c) the reactor is a fixed bed reactor, a slurry reactor or a fluid reactor;

(d) the reaction is carried out under conditions which comprise a reaction temperature within the range of 423 to 573 K, a reaction pressure within the range of 0.5 to 10.0 MPa, a volume hourly space velocity of the mixture of hydrogen and carbon monoxide within the range of 100 to 5000.

In one embodiment of the invention, said Fischer-Tropsch process is non-shifting Fischer-Tropsch process over the activated carbon supported cobalt based catalyst which promoted by a metal component wherein the metal belongs to Groups of IVB, III B, VIII B noble metal, I A or II A.

In a preferred embodiment of the invention, the metal selected from the group consisting of Ti, Zr, La, Ce, Ru, K, and Mg.

In another embodiment of the invention, about 50 wt % mixed linear alpha-alcohols having 1 to 18 carbon atoms and about 50 wt % paraffins having 1 to 25 carbon atoms are directly synthesized from Fischer-Tropsch process.

In another embodiment of the invention, the mixed linear alpha-alcohols, useful as an additive of gasoline or diesel fuel, or intermediates of detergents or plasticizers, lubricants or surfactants, contain at least 45 wt % of $C_6$ to $C_{18}$ mixed linear alpha-alcohols having an iso to normal ratio of about 0.01 to 0.1, <50 ppb by weight of sulfur and nitrogen, less than about 2 wt % of unsaturates, based on the mixed linear alpha-alcohols. In a preferred embodiment of the invention, the content of nitrogen and sulfur is less than or equal to 20 ppb by weight. In a more preferred embodiment of the invention, the content of nitrogen and sulfur is less than or equal to 10 ppb by weight.

In one embodiment of the invention, wherein the paraffins, useful as feedstocks of cracking to ethylene or feedstocks of isomerizing to gasoline or a blending component of gasoline, contains at least 95 wt % of paraffins having an iso to normal ratio of about 0.03 to 0.3, <10 ppb by weight of sulfur and nitrogen, and less than about 2 wt % unsaturates, are synthesized directly from Fischer-Tropsch process.

In another embodiment of the invention, diesel fuels, useful as diesel fuels or a blending component of diesel fuels, containing at least 95 wt % paraffins having an iso to normal ratio of about 0.03 to 0.3, <10 ppb by weight of sulfur and nitrogen, and less than about 2 wt % of unsaturates, are synthesized directly from Fischer-Tropsch process.

In a preferred embodiment of the invention, the diesel fuels have a cetane number of at least 60 to 70.

In accordance with the process of the invention, (1) mixed linear alpha-alcohols having 1 to 18 carbon atoms and being useful as an intermediate of detergents, plasticizers, lubricants, or surfactants and being useful additives of gasoline and diesel; (2) hydrocarbons having 1 to 25 carbon atoms and being useful as an excellent feedstock for naphtha crack unit to produce ethylene; and (3) and middle distillates with sulfur-free, nitrogen-free or aromatics-free and having high cetane number of at least about 60, preferably at least about 70 and being useful as a diesel fuel or as a diesel fuel blend stock, are produced, preferably direct from synthesis gas through Fischer-Tropsch process over an activated carbon supported cobalt based catalyst.

In particular, there is provided a process for preparing directly the mixed linear alpha-alcohols and the middle distillates from synthesis gas over modified Fischer-Tropsch catalysts that cut off the heavier end of the Schultz-Flory distribution.

DETAILED DESCRIPTION OF THE PREFERRED EMBODIMENT

Figure 1:
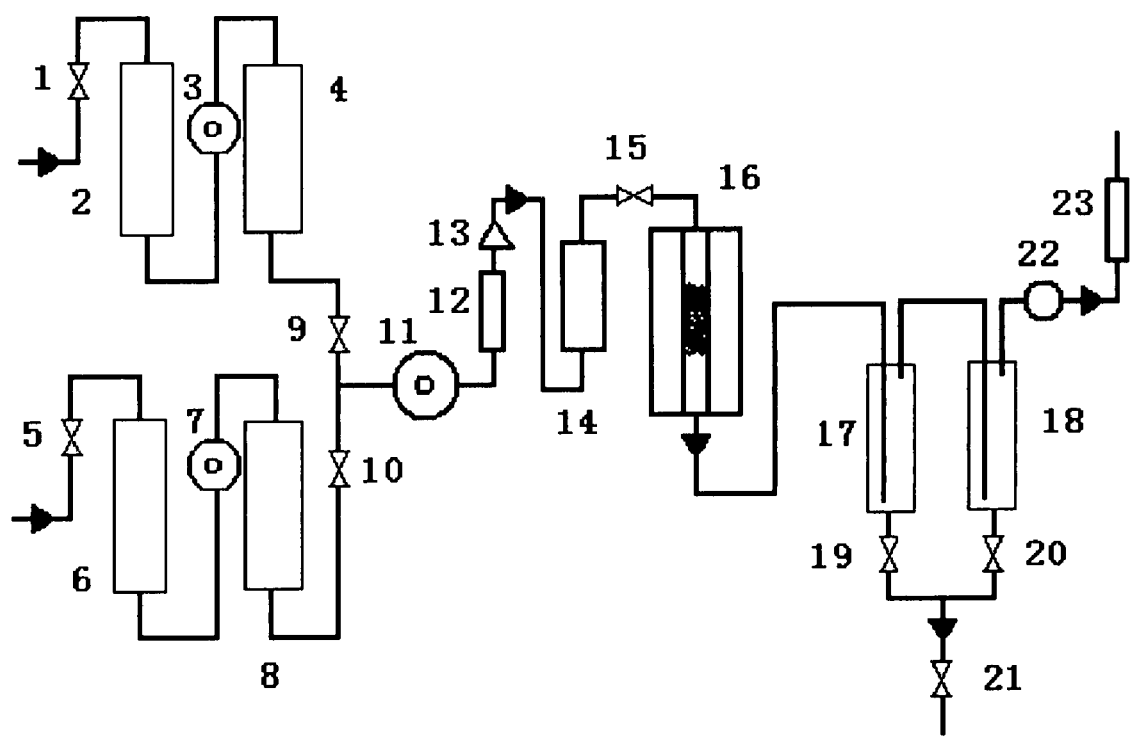
FIG. 1 is a block flow diagram representing a process for preparing mixed linear alpha-alcohols and middle distillates directly from synthesis gas over an activated carbon supported cobalt based catalyst. In the drawing: (1) stop valve; (2) purifier; (3) pressure regulator; (4) mass flow controller of carbon monoxide; (5) stop valve; (6) purifier; (7) pressure regulator; (8) mass flow controller of hydrogen; (9) stop valve; (10) stop valve; (11) mixing unit; (12) mass flow meter; (13) check valve; (14) pre-heater; (15) stop valve; (16) F-T reactor; (17) high temperature trap; (18) low temperature trap; (19) stop valve; (20) stop valve; (21) stop valve; (22) back pressure regulator; (23) float meter.

The objective of the invention is to provide a process for direct synthesis of mixed linear alpha-alcohols, naphtha distillates and diesel fuels with high quality from synthesis gas through Fischer-Tropsch synthesis, and to provide an equipment in which the Fischer-Tropsch reaction is conducted.

In order to realize the above objectives, the invention provides a process for direct synthesis of mixed linear alpha-alcohols, naphtha distillates and diesel fuels with high quality from synthesis gas through Fischer-Tropsch synthesis, wherein aliphatic alcohols, naphtha and fuels with diesel distillates as primary products are produced through one-step synthesis technique from synthesis gas, which is a mixture of hydrogen and carbon monoxide.

A synthesis gas comprising hydrogen and carbon monoxide as principal component, wherein the mole ratio of hydrogen to carbon monoxide is within the range of 1 to 3 can be produced from (1) a process of steam reforming or partial oxidation of natural gas, gas associated with oil or coal fields, or light paraffins, (2) a process of coal gasification, or (3) a process of biomass gasification. The synthesis gas can be converted into mixed linear alpha-alcohols and middle distillates over an activated carbon supported cobalt based catalyst under conditions of a reaction temperature within the range of 453 to 573 K, a reaction pressure within the range of 0.5 to 10.0 MPa, a mixture of hydrogen and carbon monoxide volume hourly space velocity within the range of 100 to 5000 $h^{-1}$.

Moreover, in the process according to the invention, the synthetic mixed linear alpha-alcohols and middle distillates can be directly synthesized through the non-shifting Fischer-Tropsch reaction over an activated carbon supported cobalt based catalyst.

In addition, in the process according to the invention, the mixed linear alpha-alcohols useful as additives for gasoline and diesel fuels, and as intermediates for a plasticizer, a detergent a lubricant, and a surfactant, comprise: (1) a fraction of $C_2$ to $C_5$ linear mixed alcohols, (2) a fraction of $C_6$ to $C_{10}$ linear mixed alcohols and (3) a fraction of $C_{11}$ to $C_{18}$ linear mixed alcohols, and can be directly synthesized from Fischer-Tropsch process, and ca. 50 wt. % $C_1$ to $C_{18}$ mixed alcohols are contained in the liquid products from the Fischer-Tropsch process, with an iso to normal ratio of about 0.001 to 0.01.

Furthermore, in the process according to the invention, the synthetic naphtha distillates useful as an excellent feedstock for naphtha crack units to produce ethylene, comprise: a fraction of $C_5$ to $C_{10}$, and can be directly synthesized from Fischer-Tropsch process, and ca. 15 wt. % $C_5$ to $C_{10}$ paraffins are contained in the total liquid products from the Fischer-Tropsch process, with an iso to normal ratio of about 0.03 to 0.3, <10 ppb by weight of sulfur and nitrogen, and less than about 2 wt. % unsaturates.

In addition, in the process according to the invention, the synthetic fuels useful as fuels heavier than gasoline or as blending components for distillate fuels, comprise: a 453 to 653 K fraction, and can be direct synthesized from Fischer-Tropsch process, and at least 35 wt. % paraffins are contained in the total liquid products from the Fischer-Tropsch process, with an iso to normal ratio of about 0.03 to 0.3, <10 ppb by weight of sulfur and nitrogen, and less than about 2 wt. % unsaturates.

Moreover, in the process according to the invention, the synthetic mixed linear alpha-alcohols and middle distillates in which the content of nitrogen and sulfur in the products is less than or equal to 10 ppb by weight, are directly synthesized from synthesis gas.

The preferred catalysts comprise a Group VIII B non-noble metal, e.g. cobalt, iron and nickel, preferably cobalt metal, in conjunction with a Group IV B metal promoter, e.g., zirconium, titanium, preferably zirconium, and a Group III B metal promoter, e.g., lanthanum, cerium, preferably lanthanum, or Group VIII B noble metal promoter, e.g., ruthenium, platinum, rhodium, preferably ruthenium, or Group I A, II A alkali or alkaline earth metal promoter, e.g., potassium, magnesium, supported on a porous support.

The porous support is preferably an activated carbon, which is made from an almond core, a coconut shell, a palm tree wood, or a coal, preferably from a coconut shell. The catalyst is prepared by co-impregnating or stepwise-impregnating the metals from solutions onto the support, drying at room temperature for 4 days, then at 353 to 363 K for 8 hours, and finally at 383 to 393 K for 10 hours.

The Group VIII B non-noble metal is present in amounts of about 40 wt % or less, preferably 5-30 wt %, while the Group IVB metal, IIIB metal, VIII B noble metal, IA alkali metal, or II A alkaline earth metal promoter(s) is/are usually present in lesser amounts, e.g., a ratio of 1:2 to about 1:200 relative to the Group VIII B non-noble metal.

In accordance with the process of the present invention, mixed linear alpha-alcohols and middle distillates are directly prepared from synthesis gas through Fischer-Tropsch process, the preferred Fischer-Tropsch process is one that utilizes a non-shifting (that is, no water gas shift capability) catalyst, such as a catalyst wherein cobalt, ruthenium or mixtures thereof, preferably cobalt is supported on an activated carbon, preferably promoted by a promoter which is zirconium, rhenium, lanthanum, or cerium, preferably zirconium and/or lanthanum.

The preferred catalyst is first reduced in a flow fixed bed reactor, a slurry reactor, or a fluid reactor, preferably a fixed bed reactor, under reduction conditions of a reduction temperature within the range of 523 to 773 K, a reduction pressure within the range of 0.3 to 1.5 MPa, a hydrogen volume hourly space velocity within the range of 100 to 2000 $h^{-1}$.

The preferred Fischer-Tropsch process is carried out in a fixed bed reactor, a slurry reactor, or a fluid reactor. If the Fischer-Tropsch process is conducted in a slurry reactor or a fluid reactor, the transfer of reduced catalyst in the protection of inert gas atmosphere such as argon or nitrogen should be necessary.

The preferred conditions for the Fischer-Tropsch process are as follows: a reaction temperature within the range of 453 to 573 K, a reaction pressure within the range of 0.5 to 10.0 MPa, a volume hourly space velocity of mixture of hydrogen and carbon monoxide within the range of 100 to 1500 $h^{-1}$, a rotation speed of an agitator in the slurry reactor within the range of 400 to 1000 r/min, and a mole ratio of hydrogen to carbon monoxide within the range of 1 to 3.

The products of the Fischer-Tropsch process are primarily linear mixed alpha-alkanols and paraffinic hydrocarbons. Ruthenium catalyst produces paraffins primarily boiling in the distillate range, i.e., $C_{10}$ to $C_{20}$, while conventional cobalt catalysts, e.g., $Co/SiO_2$, generally produce more of heavier hydrocarbons, e.g., $C_{20}^+$, and cobalt is a preferred Fischer-Tropsch catalytic metal for the production of waxes.

But an activated carbon supported cobalt based catalyst of the invention produces mixed linear alpha-alcohols having 1 to 18 carbon atoms, and paraffins having 5 to 25 carbon atoms in the liquid oil phases, and most of mixed linear alpha-alcohols fell in the range of $C_2$ to $C_{18}$, and most of paraffins are fell in the range of $C_5$ to $C_{21}$, it is believed that the shape selectivity of the pore size of Fischer-Tropsch catalyst restricts the wax formation, so the distribution of products deviates from Schultz-Folry distribution.

Non-shifting Fischer-Tropsch reactions are well known to those skilled in the art and may be characterized by conditions that minimize the formations of $CO_2$ by-products. These conditions can be achieved by a variety of methods, including one or more of the following: operating at a relatively low CO partial pressures, that is, operating at hydrogen to CO ratios of at least about 1.4/1, preferably about 1.7/1 to about 3/1, more preferably at least about 1.9/1, and in the range 1.9/1 to about 2.2/1, a temperatures of about 468 to 568 K, preferably 478 to 518 K; and using a catalyst comprising activated carbon supported cobalt or zirconium, and/or lanthanum, as the primary Fischer-Tropsch catalytic promoter.

The invention will be explained in more detail by referring to the drawing.

FIG. 1 is a block flow diagram representing a process for preparing mixed linear alpha-alcohols and middle distillates directly from synthesis gas over an activated carbon supported cobalt based catalyst.

Carbon monoxide is purified at purifier (2) where silica gel, 5 Å molecular sieves or activated carbon are filled after passing through stop valve (1), and then passed through pressure regulator (3) for controlling the inlet pressure of carbon monoxide, mass flow controller (4) for controlling the space velocity of carbon monoxide, and stop valve (9).

Hydrogen is purified at purifier (5) where silica gel, 5 Å molecular sieves or activated carbon are filled after passing through stop valve (5), and then passed through pressure regulator (7) for controlling the inlet pressure of hydrogen, mass flow controller (9) for controlling the space velocity of hydrogen, and stop valve (10).

Carbon monoxide from stop valve (9) and hydrogen from stop valve (10) are mixed in an appropriate ratio at mixing unit (11), to produce a synthesis gas.

The synthesis gas is passed through mass flow meter (12) for measuring the space velocity of synthesis gas (a mixture of hydrogen and carbon monoxide) and check valve (13) for preventing the synthesis gas from flowing back.

Thereafter, the synthesis gas is heated in pre-heater (14), and passed through stop valves (15); Fischer-Tropsch reactor (16), which may be a fixed bed reactor or a slurry reactor or a fluid reactor, wherein the synthesis gas is converted into products.

The products are sent successively to high temperature trap (17), wherein 323-653 K fraction is collected; and low temperature trap (18), wherein 0-323 K fraction is collected.

There are also stop valves (19), (20) and (21); back pressure regulator (22) for controlling the F-T reaction pressure; and float meters (23) for measuring the rate of tail gas in the equipment.

The present invention is a slurry Fischer-Tropsch synthesis process which may be conducted with from about 2 to 30 wt % or more of the catalyst suspended in liquid phase. The catalyst can be pre-treated before it is used for the process. The pretreatment is conducted usually in a separate reactor due to the low boiling point of slurry liquid. The liquid phase usually comprises an inert hydrocarbon that is relatively non-volatile under reaction conditions. Representative inert hydrocarbons include synthetic paraffins with 10 or more carbon atoms, or higher molecular weight hydrocarbons generated from the synthesis gas conversion process. Other liquid such as high boiling alcohols, ethers, esters and the like can also be used without departing from the scope of the invention.

A pretreatment in a slurry liquid involves the steps of: suspending the activated catalyst which is reduced in a flow of hydrogen in a separate fixed bed reactor, then transferring it into a slurry reactor in a flow of argon in a relatively non-volatile hydrocarbon phase, introducing hydrogen into the liquid-solid phase mixtures, and increasing the temperature up to 523~623 k so as to convert the oxidized catalyst to an active phase.

The pretreatment can be conducted at a pressure ranging from 0.3 to 1.5 Mpa, more preferably from 0.5 to about 1.0 Mpa, a hydrogen volume hourly space velocity within the range of 300 to 1500, a rotation speed of a agitator in the slurry reactor within the range of 300 to 1200 r/min.

Other preferred conditions for Fischer-Tropsch process include a reaction temperature within the range of 423 to 623 K, a reaction pressure within the range of 0.5 to 10.0 MPa, a volume hourly space velocity of mixture of hydrogen and carbon monoxide within the range of 100 to 1500 h$^{-1}$, a rotation speed of the agitator in the slurry reactor within the range of 400 to 1200 r/min, and a mole ratio of hydrogen to carbon monoxide within the range of 1 to 3.

Hydrogen and carbon monoxide synthesis gas (H$_2$/CO=1.95-2.15) are converted to linear mixed alcohols and middle distillate paraffins in a Fischer-Tropsch reactor, which may be a fixed bed reactor, a slurry reactor, a fluid reactor. The catalyst used for the Fischer-Tropsch process is an activated carbon supported cobalt/zirconium/lanthanum catalyst. Most preferably, the reaction conditions are about 493 K, 2.0 MPa, and GHSV=1300 h$^{-1}$. The sample had been collected for 50 hours from TOS (time on stream)=24 hours.

The invention will be illustrated by the following examples, but not limited thereto.

EXAMPLE 1

Fischer-Tropsch reaction was carried out on the equipment illustrated in FIG. 1. a cobalt based catalyst, 15Co1Zr0.5La/AC (AC representing Activated Carbon which was made from a coconut shell), was employed to produce the mixed linear alpha-alcohols and middle distillate paraffins from synthesis gas in a fixed bed reactor (i.d.=9 mm, h=35 cm). 4 ml (2.1 grams, 0.3-0.5 mm) of the cobalt based catalyst was loaded into the reactor. 15Co1Zr0.5La/AC catalyst was first in-situ reduced in the fixed bed reactor using 10% H$_2$/90% N$_2$ mixture gas under conditions of P=0.1 Mpa, GHSV=1000 h$^{-1}$, the activation temperature being increased from room temperature to 623 K at 5 K/min, and kept at 623 K for 12 hours before reaction. Then, the reactor was cooled down to 423 K after finishing the catalyst reduction, then fed with synthesis gas having a H$_2$/CO ratio=2 from 10% H$_2$90% N$_2$ at 423 K, and the pressure of synthesis gas was increased from atmosphere to 2.0 Mpa and the volume hourly space velocity of synthesis gas was set to 1300 h$^{-1}$, and finally the reaction temperature was slowly increased to 493 K. The liquid sample had been collected in the traps (17) and (18) for 50 hours after TOS=24 hours, and the tail gas was analyzed hourly on-line by using Agilent 3000A Micro-GC. The results were summarized in Table 1.

EXAMPLE 2

The same procedures as in example 1 were repeated, except for the reduction temperature of 723 K instead of 623 K being used. The results were summarized in Table 1.

EXAMPLE 3

The same procedures as in example 2 were repeated, except for the reduction was conducted in a quartz fixed bed reactor instead of the same Fischer-Tropsch reactor, and the reduced catalyst was very carefully transferred from the quartz reactor into the Fischer-Tropsch reactor (a fixed bed reactor) under a flow of argon to prevent the air. The results were summarized in Table 1.

EXAMPLE 4

The same procedures as in example 1 were repeated, except for a slurry reactor instead of the fixed bed reactor being used, the catalyst being reduced in a quartz fixed bed reactor instead of being in-situ reduced in the Fischer-Tropsch reactor, and the reduced catalyst was very carefully transferred from the quartz reactor into Fischer-Tropsch slurry reactor in a flow of argon to prevent the air, and except for 20 ml (10.5 grams, 0.2~2.0 μm) 15Co1Zr0.5La/AC catalyst being loaded instead of 4 ml (2.1 grams, 0.3-0.5 mm) the catalyst and a liquid paraffin was used as the slurry liquid. The results were summarized in Table 1.

EXAMPLE 5

The same procedures as in example 2 were repeated, except for a reaction pressure of 3.0 Mpa instead of 2.0 Mpa being used. The results were summarized in Table 1.

EXAMPLE 6

The same procedures as in example 1 were repeated, except for a reaction pressure of 4.0 Mpa instead of 2.0 Mpa being used. The results were summarized in Table 1.

EXAMPLE 7

The same procedures as in example 1 were repeated, except for a volume hourly space velocity of 2600 h$^{-1}$ instead of 1300 h$^{-1}$ being used. The results were summarized in Table 1.

EXAMPLE 8

The same procedures as in example 7 were repeated, except for GHSV of 3900 h$^{-1}$ instead of 2600 h$^{-1}$ being used. The results were summarized in Table 1.

EXAMPLE 9

The same procedures as in example 1 were repeated, except for a catalyst particle size of 1~3 mm instead of 0.3~0.5 mm being used. The results were summarized in Table 1.

EXAMPLE 10

The same procedures as in example 1 were repeated, except for a reaction temperature of 510 K instead of 490 K being used. The results were summarized in Table 1.

EXAMPLE 11

The same procedures as in example 1 were repeated, except for a reaction temperature of 518 K instead of 490 K being used. The results were summarized in Table 1.

EXAMPLE 12

The same procedures as in example 4 were repeated, except for a reduction temperature of 723 K instead of 623 K and GHSV of 500 h$^{-1}$ instead of 1300 h$^{-1}$ being used. The results were summarized in Table 1.

EXAMPLE 13

The same procedures as in example 12 were repeated, except for a reaction pressure of 3.0 Mpa instead of 2.0 Mpa being used. The results were summarized in Table 1.

EXAMPLE 14

The same procedures as in example 12 were repeated, except for a fluid reactor instead of the slurry reactor and a particle size of 0.05-0.2 mm instead of 0.2-2 μm being used. The results were summarized in Table 1.

TABLE 1

Results of Fischer-Tropsch reaction over 15Co1Zr0.5La/AC catalyst under various reactors and different reaction conditions*

| Example | CO Conversion, % | Selectivity mol % | | | | | Distribution of liquid products, wt.% | | | |
|---|---|---|---|---|---|---|---|---|---|---|
| | | $CH_4$ | $CO_2$ | Alcohol | olefin | paraffin $C_2^+$ | methanol | $C_{2-18}$alcohols | olefin | paraffin |
| 1 | 22.3 | 33.5 | 2.7 | 27.5 | 11.4 | 24.9 | 9.0 | 63.1 | 1.3 | 26.6 |
| 2 | 58.2 | 13.3 | 3.9 | 42.6 | 10.3 | 29.9 | 8.7 | 61.1 | 1.5 | 28.7 |
| 3 | 21.9 | 32.1 | 3.2 | 27.8 | 13.0 | 23.9 | 9.3 | 63.8 | 1.2 | 25.7 |
| 4 | 18.2 | 18.6 | 3.3 | 32.5 | 11.7 | 33.9 | 9.5 | 62.7 | 1.0 | 26.8 |
| 5 | 43.0 | 31.7 | 2.8 | 27.4 | 12.8 | 25.3 | 9.1 | 63.5 | 1.3 | 26.1 |
| 6 | 54.7 | 30.2 | 2.4 | 28.4 | 12.5 | 26.5 | 8.7 | 64.9 | 1.3 | 25.1 |
| 7 | 19.4 | 30.8 | 2.9 | 29.6 | 12.3 | 24.4 | 8.6 | 65.6 | 1.2 | 24.6 |
| 8 | 14.3 | 29.4 | 2.9 | 31.3 | 12.2 | 24.2 | 8.5 | 65.8 | 1.1 | 24.6 |
| 9 | 20.0 | 30.9 | 2.6 | 28.1 | 13.9 | 24.5 | 12.4 | 64.7 | 0.8 | 22.1 |
| 10 | 42.2 | 31.2 | 4.7 | 26.9 | 13.9 | 23.3 | 8.7 | 59.5 | 3.2 | 28.6 |
| 11 | 51.2 | 38.0 | 5.8 | 25.1 | 13.1 | 29.0 | 6.8 | 54.3 | 4.8 | 34.1 |
| 12 | 51.2 | 12.0 | 1.8 | 40.1 | 9.1 | 37.0 | 6.1 | 47.0 | 4.8 | 42.1 |
| 13 | 55.2 | 11.8 | 1.5 | 44.7 | 6.1 | 35.8 | 6.7 | 52.3 | 2.8 | 38.2 |
| 14 | 65.2 | 19.0 | 1.9 | 42.5 | 3.1 | 33.5 | 5.8 | 52.3 | 5.8 | 36.1 |

*The sample had been collected for 50 hours from TOS = 24 hours.

What is claimed is:

1. A process for directly producing mixed linear alpha-alcohols having 1 to 18 carbon atoms from synthesis gas comprising hydrogen and carbon monoxide, comprising the step of
   reacting hydrogen and carbon monoxide over a catalyst to produce mixed linear alpha-alcohols having 1 to 18 carbon atoms and hydrocarbons having 1 to 25 carbon atoms through a Fischer-Tropsch process in one step in a reactor, wherein:
   (a) the molar ratio of hydrogen to carbon monoxide is within the range of 1 to 3;
   (b) the catalyst is an activated carbon supported cobalt/zirconium/lanthanum catalyst, wherein the activated carbon is made from coconut shell;
   (c) the reactor is a fixed bed reactor, a slurry reactor or a fluid reactor; and
   (d) the reaction is carried out under conditions of a reaction temperature within the range of 423 to 573 K, a reaction pressure within the range of 0.5 to 10.0 MPa, and a volume hourly space velocity of the mixture of hydrogen and carbon monoxide within the range of 100 to 5000.

2. The process of claim 1, wherein about 50 wt % mixed linear alpha-alcohols having 1 to 18 carbon atoms and about 50 wt % paraffins having 1 to 25 carbon atoms are directly synthesized from the Fischer-Tropsch process.

3. The process of claim 2, wherein the mixed linear alpha-alcohols contain at least 45 wt % of C6 to C18 mixed linear alpha-alcohols having an iso to normal ratio of about 0.01 to 0.1, <50 ppm by weight of sulfur and nitrogen, less than about 1 wt % of unsaturates, based on the mixed linear alpha-alcohols.

4. The process of claim 2, wherein the paraffins contain at least 95 wt % of paraffins having an iso to normal ratio of about 0.03 to 0.3, <10 ppb by weight of sulfur and nitrogen, and less than about 2 wt % unsaturates, based on the paraffins.

5. The process of claim 3, wherein the content of nitrogen and sulfur is less than or equal to 10 ppb by weight.

6. The process of claim 5, wherein the content of nitrogen and sulfur is less than or equal to 10 ppb by weight.

7. The process of claim 1, wherein at least about 47% wt % mixed linear alpha-alcohols having 1 to 18 carbon atoms are directly synthesized from the Fischer-Tropsch process.

* * * * *

UNITED STATES PATENT AND TRADEMARK OFFICE
CERTIFICATE OF CORRECTION

PATENT NO. : 7,468,396 B2  Page 1 of 1
APPLICATION NO. : 11/890772
DATED : December 23, 2008
INVENTOR(S) : Ding et al.

It is certified that error appears in the above-identified patent and that said Letters Patent is hereby corrected as shown below:

At column 7, line 57, please delete "Folry" and insert therefore, --Flory--.

Signed and Sealed this

Ninth Day of June, 2009

JOHN DOLL
*Acting Director of the United States Patent and Trademark Office*